United States Patent [19]
Imai et al.

[11] Patent Number: 5,695,718
[45] Date of Patent: Dec. 9, 1997

[54] AUTOMATIC ANALYZER

[75] Inventors: Kyoko Imai; Kazumichi Imai, both of Hitachinaka; Yasushi Nomura, Mito, all of Japan

[73] Assignee: Hitachi, Ltd., Tokyo, Japan

[21] Appl. No.: 405,345

[22] Filed: Mar. 16, 1995

[30] Foreign Application Priority Data

Mar. 18, 1994 [JP] Japan ................... 6-048583

[51] Int. Cl.6 .................. G01N 35/02; G08B 1/08
[52] U.S. Cl. ............... 422/62; 422/63; 422/64; 422/65; 422/67; 436/50; 436/55; 364/496; 340/521; 340/531; 340/539; 340/576
[58] Field of Search ............. 436/50, 55; 422/62, 422/63, 64, 65, 67, 98; 364/497, 498, 496; 340/539, 521, 531, 576

[56] References Cited

U.S. PATENT DOCUMENTS

| | | | |
|---|---|---|---|
| 4,313,735 | 2/1982 | Yamashita et al. | 422/65 X |
| 4,647,432 | 3/1987 | Wakatake | 422/64 |
| 4,665,385 | 5/1987 | Henderson | 340/539 |
| 4,731,225 | 3/1988 | Wakatake | 422/65 |

FOREIGN PATENT DOCUMENTS

| | | |
|---|---|---|
| 350049 | 1/1990 | European Pat. Off. . |
| 4312093 | 10/1993 | Germany . |
| 57-120115 | 7/1982 | Japan . |
| 59-109992 | 6/1984 | Japan . |
| 2-52593 | 2/1990 | Japan . |
| 4-1570 | 1/1992 | Japan . |
| 4-367098 | 12/1992 | Japan . |
| 2194119 | 2/1988 | United Kingdom . |
| 2201272 | 8/1988 | United Kingdom . |

*Primary Examiner*—Harold Pyon
*Attorney, Agent, or Firm*—Matthew G. Reeves

[57] ABSTRACT

An automatic analyzer in which a suitable transmission destination remote from a body of the automatic analyzer is selected in accordance with the contents of to be transmitted and the contents are transmitted to the transmission destination; a suitable operation control instruction is received from a suitable person on duty; and a suitable process is carried out to make it possible to improve analysis efficiency.

1 Claim, 6 Drawing Sheets

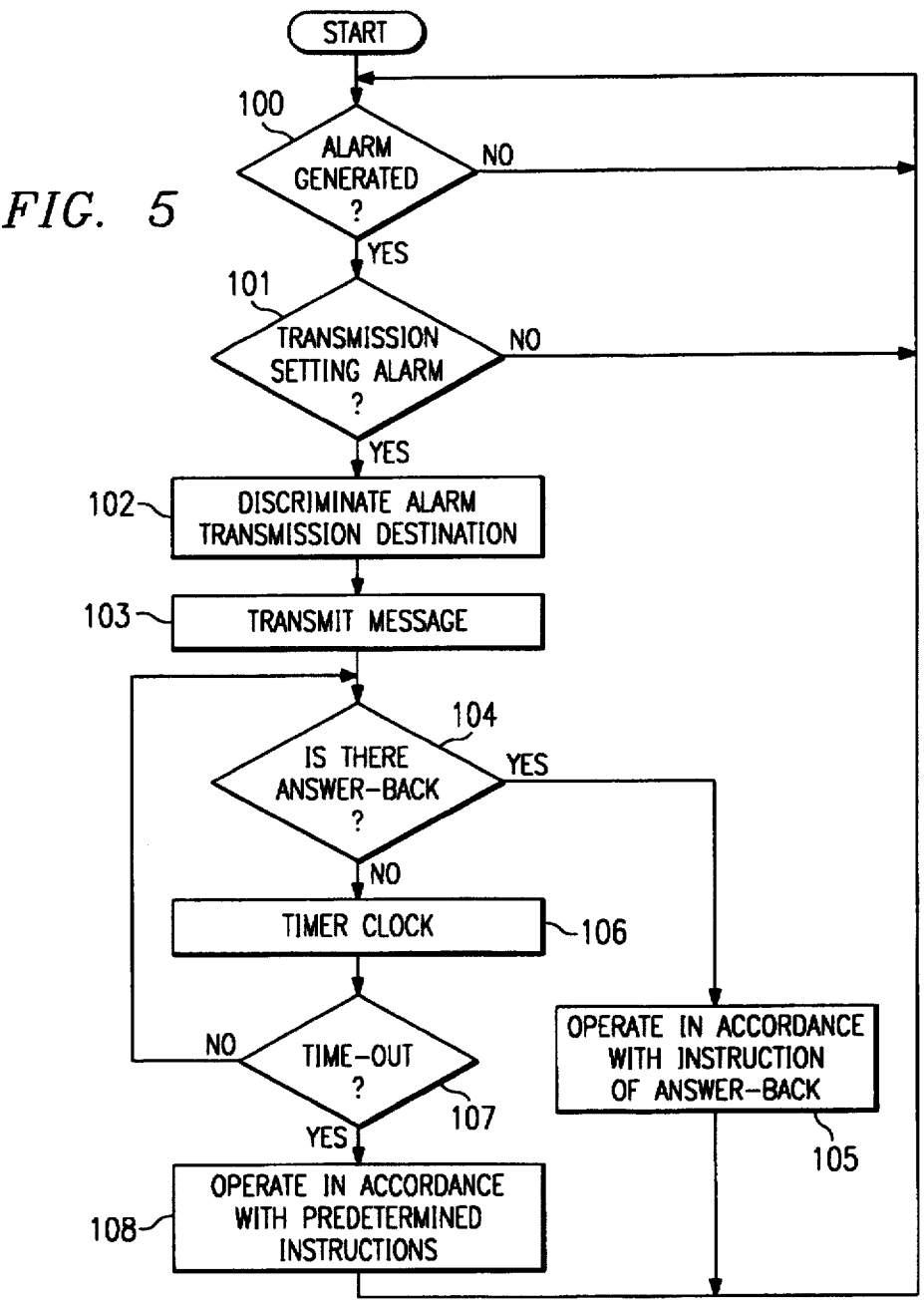

FIG. 7A

| A/S NO.83 |
| A/REAGN/CALIB |
| A/15 |

| B/S NO.115 |
| B/SAMPL |

| A/6, B/11 |

— 42B

| ALARM NAMES | CODE | MESSAGE | TRANSMISSION DESTINATION |
|---|---|---|---|
| INSUFFICIENT SAMPLE | 1-a | SAMPL | OPERATOR |
| INSUFFICIENT REAGENT | 1-b | REAGN | OPERATOR |
| INSUFFICIENT CLEANER | 1-c | CLEAN | OPERATOR |
| INSUFFICIENT SUPPLY WATER | 1-d | WATER | OPERATOR |
| CALIBRATION DATA ERROR | 2-A,B,C,D | CALIB | PERSON IN CHARGE OF DATA |
| CONTROL DATA ERROR | 3 | QC | PERSON IN CHARGE OF DATA |
| WASHING MECHANISM ERROR | 5 | WASH | PERSON IN CHARGE OF MAINTENANCE |
| REACTION DISK ERROR | 6 | | PERSON IN CHARGE OF MAINTENANCE |
| SAMPLE DISK ERROR | 7 | | PERSON IN CHARGE OF MAINTENANCE |
| REAGENT DISK ERROR | 8 | | PERSON IN CHARGE OF MAINTENANCE |
| SAMPLE PROBE ERROR | 9 | | PERSON IN CHARGE OF MAINTENANCE |
| REAGENT PROBE ERROR | 10 | | PERSON IN CHARGE OF MAINTENANCE |
| SAMPLE SYRINGE ERROR | 11 | | PERSON IN CHARGE OF MAINTENANCE |
| REAGENT SYRINGE ERROR | 12 | | PERSON IN CHARGE OF MAINTENANCE |
| INCUBATOR WATER TEMPERATURE ERROR | 13-A | | PERSON IN CHARGE OF MAINTENANCE |
| INCUBATOR WATER LEVEL ERROR | 13-B | | PERSON IN CHARGE OF MAINTENANCE |
| ABNORMAL INSTRUMENT TEMPERATURE | 14 | TEMP | OPERATOR |
| MALFUNCITON OF MIXING MECHANISM | 15 | | PERSON IN CHARGE OF MAINTENANCE |
| PHOTOMETER ERROR | 16 | | PERSON IN CHARGE OF MAINTENANCE |
| MALFUNCTION OF PRINTER | 17 | | PERSON IN CHARGE OF MAINTENANCE |
| END OF SAMPLING | 18 | S.STOP | OPERATOR |
| END OF ANALYSIS | 19 | END | OPERATOR |
| FUSE BLOWN | 20 | | PERSON IN CHARGE OF MAINTENANCE |
| MOTOR CONTROL ERROR | 21 | | PERSON IN CHARGE OF MAINTENANCE |
| MOTOR TIME-OUT | 22 | | PERSON IN CHARGE OF MAINTENANCE |
| INSUFFICIENT ELECTROLYTE REAGENT | 23 | E.REAG | OPERATOR |
| ELECTROLYTE NOZZLE ERROR | 24 | | PERSON IN CHARGE OF MAINTENANCE |

FIG. 6

AUTOMATIC ANALYZER

BACKGROUND OF THE INVENTION

The present invention relates to an automatic analyzer for analyzing blood, urine, and so on.

As an example of conventional automatic analyzers, there is an automatic analyzer described in JP-A 4-1570. In the conventional automatic analyzer, the automatic analyzer is formed so that occurrence of abnormality is transmitted to an alarm reception notification means arranged in a remote place to thereby be notified to an operator or the like in the case where any operational abnormality has occurred when the automatic analyzer is in an unmanned operation without supervision of any operator or the like. In this manner, the operator or the like can take measures properly even in the unmanned operation of the automatic analyzer when operational abnormality has occurred in the automatic analyzer.

The following means are examples of remote information communication means at the time of abnormality in the conventional automatic analyzer though the following means are not applied to automatic analyzers.

Firstly, a building remote supervising system has been described in JP-A 2-52593. In the system, a building equipment supervising apparatus transmits a signal indicating the name of a building and the contents of abnormality to a wireless apparatus located in a remote place when abnormality has occurred in equipment of the building. The building name and the contents of abnormality are displayed by the wireless apparatus, so that a person in charge of maintenance carries out a suitable operation in accordance with the contents displayed.

Secondly, a process supervising apparatus has been described in JP-A 59-109992. In the apparatus, an oscillation signal from an oscillator is transmitted to a receiver located in a remote place when a failure has occurred in a process equipment. Upon reception of the oscillation signal, the receiver generates a reception sound so that a person in charge of maintenance recognizes the occurrence of failure from the reception sound.

Thirdly, a remote alarm notification apparatus in automatic operation system supervision has been described in JP-A 57-120115. In the alarm notification apparatus, when an alarm signal is generated from an automatic operation system, a command corresponding to the alarm signal is read from a storage device. The command contains a voice signal expressing an alarm in speech, and a signal indicating the telephone number of a liaison place. The telephone circuit is connected to the telephone number of the liaison place, so that an alarm voice based on the voice signal through a telephone to which the telephone circuit is connected is transmitted to a person in charge of supervision.

Fourthly, an abnormality notification apparatus has been described in JP-A 4-367098. In the apparatus, telephone numbers and messages with respect to a plurality of persons concerned are stored in a storage section in accordance with the classification of abnormality. When abnormality has occurred, a message corresponding to the classification of the abnormality and a telephone number are selected from the messages and telephone numbers with respect to the plurality of persons concerned, so that the selected message is transmitted to a person of the selected telephone number.

Recently there are circumstances in which such an automatic analyzer of this type is large-sized so that a large number of samples are arranged at the same time in the apparatus or one operator operates and supervises a plurality of automatic analyzers of this type simultaneously, for the purpose of analyzing a large number of samples efficiently. In such circumstances, the operator cannot always stay in the side of a specific apparatus, so that there arises a time in which the operator is apart from the apparatus side.

Accordingly, when abnormality has occurred in a certain automatic analyzer in the case where one operator supervises a plurality of automatic analyzers, the operator must recognize the occurrence of abnormality and must approach the apparatus in which abnormality has occurred. Accordingly, the abnormality is left for the time required for the operator's recognizing the occurrence of abnormality and for the time required for the operator's approaching the abnormal apparatus and starting the work for recovering the abnormality.

Further, for example, in the case where addition of reagents is needed, the operator may go to a storehouse away from a room where the automatic analyzer is placed or may do distributive sample suction and injection work in another working room to prepare for the next analysis. Even when abnormality occurs in the automatic analyzer and an alarm sound for informing of the abnormality is generated from a body of the apparatus in this case, a large time is required for the operator's recognizing the abnormality so that the abnormality is left for the large time.

It is therefore convenient that the automatic analyzer operator can grasp the analysis progressive state of the automatic analyzer timely in a remote place. For example, if the operator can grasp the fact that only one sample is not analyzed yet in case of occurrence of abnormality in the automatic analyzer, the operator can continue the analysis without stopping the analysis operation. For example, if the operator can grasp the fact that a time not smaller than two hours will be required until the next sample addition when the automatic analyzer is in a normal operation, the operator can carry out another work. When sample addition will be required after about ten minutes from now, the operator can stop the other work to prepare for the next analysis.

Further, abnormality of the automatic analyzer is diversified. For example, there are abnormality concerned with trouble of analysis data of a patient or a subject to be tested, abnormality concerned with trouble of calibration data, abnormality concerned with trouble of control data, abnormality concerned with abnormality of respective hard units in the apparatus, abnormality concerned with trouble of communication with a host CPU, etc.

The abnormality of the automatic analyzer is classified into abnormality which can be dealt with by the operator and abnormality which cannot be dealt with by the operator. For example, it is said that abnormality such as short supply of analysis reagents or analysis purified water, or the like, is to be dealt with by the apparatus operator whereas abnormality concerned with trouble of calibration data or control data is to be dealt with not by the apparatus operator but by a person in charge of a room for clinical examinations because the abnormality contains important contents exerting an influence upon reliability on analysis data of a patient. Further, abnormality of hard units is to be dealt with not by the apparatus operator and the person in charge of a room for clinical examinations but by a person in charge of maintenance of the apparatus.

Accordingly, in the case where abnormality to be dealt with by other persons in charge than the apparatus operator has occurred, conventionally, the apparatus operator must determine who is a person suitable for dealing with the abnormality and must transmit the occurrence of the abnormality to the person by any suitable means. As a result, the operation of a plurality of automatic analyzers by the apparatus operator is interrupted so that the analysis efficiency of the automatic analyzers is lowered.

It is therefore thought of that the supervising apparatus as described in JP-A 2-52593, JP-A 59-109992 and JP-A 57-120115 is applied to the automatic analyzer as described in JP-A 4-1570.

Even in the case where the supervising apparatus is applied to the automatic analyzer, the occurrence of abnormality is however transmitted to respective persons in charge equally irrespective of the contents of the abnormality. Accordingly, the apparatus operator must still determine the most suitable person in charge and must transmit the occurrence of the abnormality to the person in the same manner as described above, so that the analysis efficiency of the automatic analyzer is lowered.

It is therefore thought of that the abnormality notification apparatus described in JP-A 4-367098 is applied to the automatic analyzer described in JP-A 4-1570. In this case, the occurrence of abnormality can be transmitted to the most suitable person in charge in accordance with the contents of the abnormality but the most suitable person in charge cannot take proper measures unless the person informed of the occurrence of the abnormality moves from the place where the person is informed thereof to the place where the abnormal automatic analyzer is arranged. Accordingly, the analysis efficiency of the automatic analyzer is lowered by the time required for the movement.

An object of the present invention is to provide an automatic analyzer in which: a suitable transmission destination remote from a body of the automatic analyzer is selected in accordance with contents to be transmitted so that the contents are transmitted to the selected transmission destination; a suitable operation control instruction is received from a suitable person in charge; and a suitable process is carried out in accordance with the operation control instruction to make it possible to improve analysis efficiency.

SUMMARY OF THE INVENTION

To achieve the foregoing object, the present invention is configured as follows.

An automatic analyzer for analyzing a sample such as blood, urine, or the like, includes: a determining section for determining whether a predetermined state to be transmitted has occurred in a period of an analyzing operation or not; a transmission destination discrimination section for discriminating a predetermined transmission destination located in a remote place from the automatic analyzer and a predetermined transmission message in accordance with the state which has occurred when the determining section makes a decision that the state to be transmitted has occurred; a transmission section for transmitting a signal expressing the transmission message; and a reception section for receiving a command signal from the transmission destination and supplying the command signal to the determining section, so that the determining section controls the analyzing operation in accordance with the command signal supplied by the reception section.

In the automatic analyzer, preferably, the signal transmitted to the transmission destination by the transmission section is a wireless signal.

In the automatic analyzer, preferably, the transmission destination is constituted by a plurality of portable transceivers.

In the automatic analyzer, preferably, the transmission section transmits a signal expressing a predetermined transmission source code as well as the signal expressing the transmission message.

In the automatic analyzer, preferably, each of the portable transceivers preferably includes a reception portion for receiving the signal transmitted by the transmission section of the automatic analyzer, a display portion for displaying the message expressed by the received signal, an operation portion for setting an operator's instruction, an instruction signal generation portion for generating a signal expressing the instruction set by the operation portion, and a transmission portion for transmitting the signal generated by the instruction signal generation portion to the reception section of the automatic analyzer.

In the automatic analyzer, preferably, the determining section controls the analyzing operation in accordance with a predetermined instruction when the determining section does not receive the command signal from the transmission destination in a predetermined time after the transmission message is transmitted by the transmission section.

Preferably, the automatic analyzer preferably further includes a transmission message setting section for setting a state to be transmitted and a transmission message in accordance with an operation by an operator, and a message storage section for storing the transmission message set by the transmission message setting section for every state to be transmitted.

In the automatic analyzer, preferably, the transmission message setting section further sets a destination of transmission of the transmission message in accordance with the operation by the operator, and the message storage section stores the transmission message and the transmission destination for every state to be transmitted.

The automatic analyzer preferably further includes a display means for displaying the contents set by the message setting section.

In the automatic analyzer, preferably, the message displayed on the display portion of the portable transceiver contains a code corresponding to a state to be transmitted.

In the automatic analyzer, preferably, the transmission section of the automatic analyzer preferably transmits a signal indicating a transmission destination as well as the transmission message.

In the automatic analyzer, preferably, the transmission destination discrimination section discriminates the transmission destination and the message indicating an operation progressive state whenever a predetermined process of the analysis operation is completed, and the transmission section transmits the transmission destination and the operation progressive state message discriminated by the transmission destination discrimination section whenever the predetermined process is completed.

In the automatic analyzer, preferably, the transmission destination discrimination section discriminates the transmission destination and the message indicating an operation progressive state at intervals of a predetermined time, and the transmission section transmits a signal indicating the transmission destination and the operation progressive state message discriminated by the transmission destination discrimination section at intervals of the predetermined time.

In the automatic analyzer, preferably, the transmission destination discrimination section discriminates the transmission destination and a preliminarily set normal operation message whenever a predetermined process of the analysis operation is completed, in the case where a decision is made by the determining section that there is no state to be transmitted, and the transmission section transmits a signal indicating the transmission destination and the normal operation message discriminated by the transmission destination discrimination section whenever the predetermined process is completed, in the case where a decision is made by the determining section that there is no state to be transmitted.

In the automatic analyzer, preferably, the transmission destination discrimination section discriminates the transmission destination and a predetermined normal operation message at intervals of a predetermined time, in the case where a decision is made by the determining section that there is no state to be transmitted, and the transmission section transmits a signal indicating the transmission destination and the normal operation message discriminated by the transmission destination discrimination section at intervals of the predetermined time, in the case where a decision is made by the determining section that there is no state to be transmitted.

In the automatic analyzer, preferably, the state to be transmitted includes an abnormal state of the automatic analyzer, the transmission destination discrimination section discriminates the transmission destination and a predetermined abnormality message whenever a predetermined process of the analysis operation is completed, in the case where a decision is made by the determining section that the automatic analyzer is in an abnormal state, and the transmission section transmits a signal indicating the transmission destination and the abnormality message discriminated by the transmission destination discrimination section whenever the predetermined process is completed, in the case where a decision is made by the determining section that the automatic analyzer is in an abnormal state.

In the automatic analyzer, preferably, the state to be transmitted includes an abnormal state of the automatic analyzer, the transmission destination discrimination section discriminates the transmission destination and a preliminarily set abnormality message at intervals of a predetermined time, in the case where a decision is made by the determining section that the automatic analyzer is in an abnormal state, and the transmission section transmits a signal indicating the transmission destination and the abnormality message discriminated by the transmission destination discrimination section at intervals of the predetermined time, in the case where a decision is made by the determining section that the automatic analyzer is in an abnormal state.

When a state to be transmitted, such as abnormality, or the like, occurs in a period of an analysis operation of the automatic analyzer, the occurrence of the state is determined by the determining section. Further, the transmission destination discrimination section discriminates a message indicating the occurrence of the state and a transmission destination located in a remote place where the message is to be transmitted. The transmission section transmits a signal indicating the message and the transmission destination thus discriminated. Upon reception of the message, a person in charge in the transmission destination transmits an instruction signal to the reception section of the automatic analyzer in accordance with the message. Upon reception of the instruction signal from the transmission destination, the reception section of the automatic analyzer supplies the received signal to the determining section. The determining section controls the operation of the automatic analyzer in accordance with the supplied instruction signal. In this manner, a suitable operation is carried out rapidly when an abnormal state occurs in a period of an analysis operation, so that analysis operation interruption time can be shortened.

Further, in the case where the instruction signal is not received from the transmission destination in a predetermined time after the transmission section of the automatic analyzer transmits a transmission message, the determining section controls the analysis operation in accordance with a preliminarily set instruction. In this manner, a suitable control operation can be carried out even in the case where any trouble occurs in the transmission destination.

Further, the state to be transmitted, the transmission message and the transmission destination are stored in the message storage section by the transmission message setting section in accordance with the operator's operation. In this manner, message transmission can be carried out in accordance with requests in respective facilities in which automatic analyzers are set up.

Further, the transmission destination discrimination section discriminates an operation progressive state message or a normal operation message and a transmission destination whenever a predetermined process of an analysis operation is completed or at intervals of a predetermined time. A signal indicating the transmission destination and the operation progressive state message or the normal operation message thus discriminated is transmitted by the transmitter section. In this manner, a person in charge in the transmission destination can recognize the progressive state of the analysis operation, and so on.

BRIEF DESCRIPTION OF THE DRAWINGS

FIG. 5 is an operational flow chart in the embodiment of FIG. 1.

FIG. 6 is a view showing an example of correspondence between alarm name, alarm code, message and transmission destination.

FIGS. 7A–C are a view showing examples of messages indicated on display portions of the transceivers.

FIG. 8 is a view showing an example of a display screen for setting alarm messages and transmission destinations.

Figure 1:
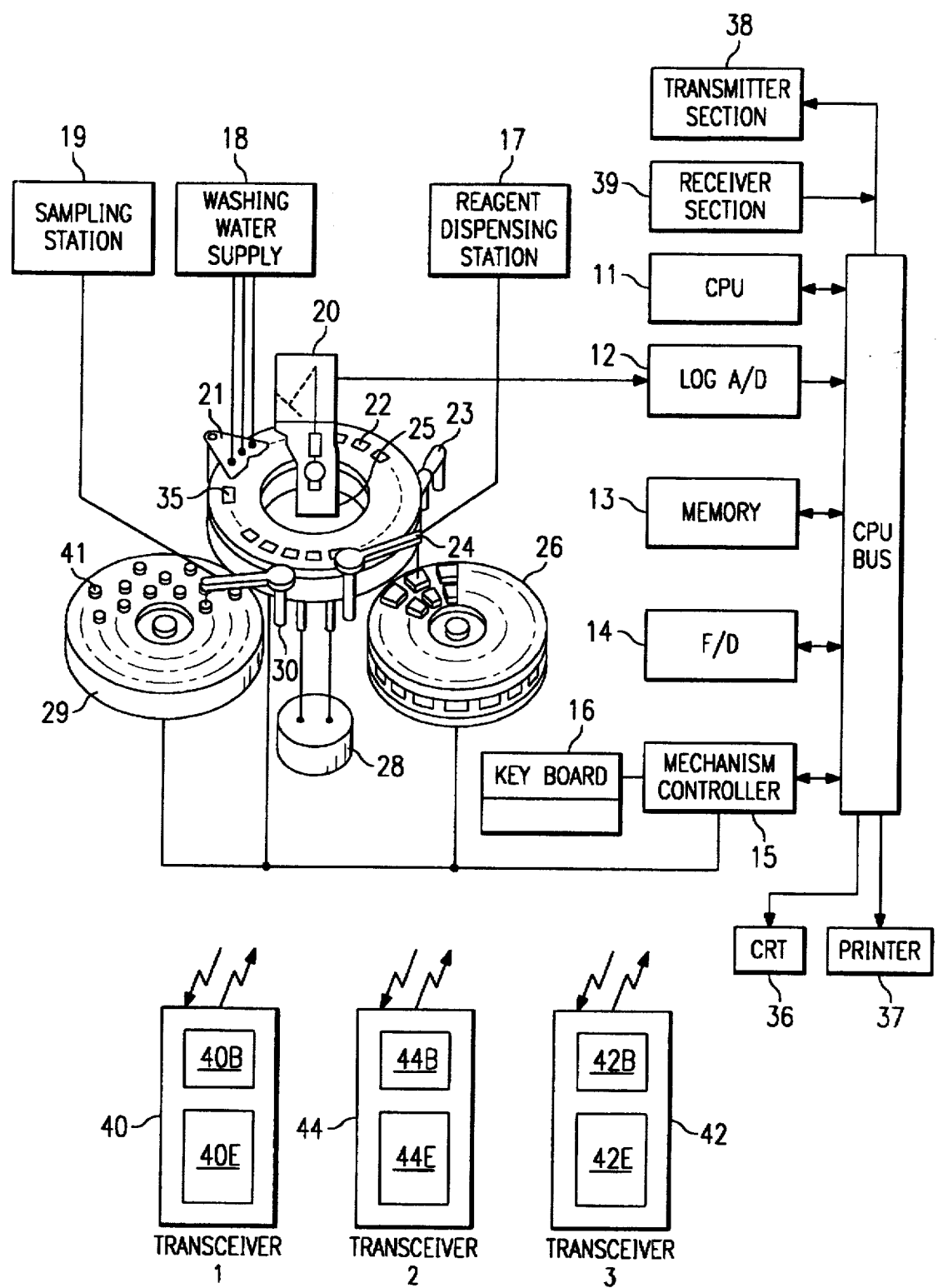
FIG. 1 is an overall schematic structural diagram of an embodiment of the present invention.

1 Chemistry unit of Automatic Analyzer
10 CPU bus
11 control CPU
11A operation control section
11B transmission destination and message setting section
11C storage section for storing messages for every transmission destination
11D transmission destination setting section
11E counter
11F answer-back discrimination section
12 LOG amplifier and A/D converter
13 memory
14 floppy disk drive 15 mechanism controller section
16 keyboard
17 reagent dispensing station
18 washing water supply
19 sampling station
20 photometer
21 washing mechanism
22 reaction disk
23 stirring mechanism
24 reagent pipetting mechanism
25 light source
26 reagent vessel
27 reagent disk
28 isothermal tank
29 sample disk
30 sample pipetting mechanism
35 reactor
36 CRT
37 printer
38 transmitter section
39 receiver section
40 transceiver (1)
41 sample vessel
42 transceiver (3)
44 transceiver (2)
40A, 42A, 44A receiver portion
40B, 42B, 44B message display portion
40C, 42C, 44C instruction signal generation portion
40D, 42D, 44D transmitter portion
40E, 42E, 44E operation portion

DETAILED DESCRIPTION OF EMBODIMENTS OF THE INVENTION

Figure 2:
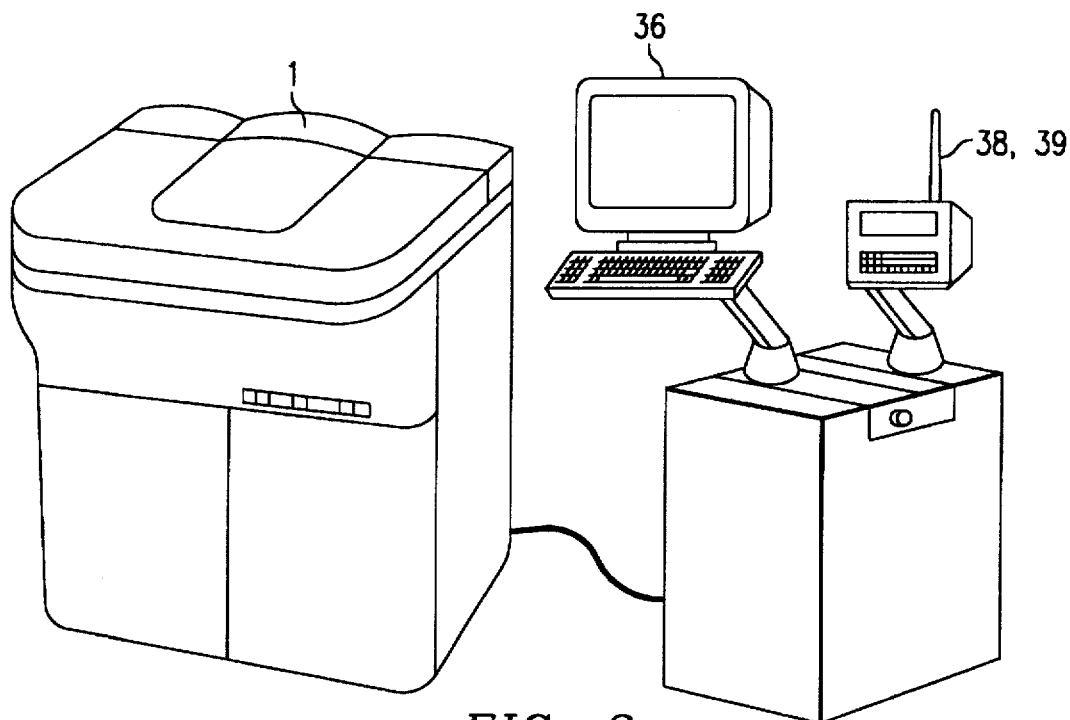
FIG. 2 is an exterior view of the embodiment of the present invention.

FIG. 1 is a schematic structural diagram of an embodiment of an automatic analyzer according to the present invention, and FIG. 2 is an exterior view of the embodiment of FIG. 1.

In FIGS. 1 and 2, the automatic analyzer includes a control CPU (central processing unit) 11, a LOG amplifier and an analog-to-digital (A/D) converter 12, a memory 13, a floppy disk drive 14, a keyboard 16, a mechanism control section 15, a cathode ray tube (CRT) 36 for displaying measurement results, an operation screen, or the like, and a printer 37 for printing measurement results, or the like. These constitutional elements 12, 13, 14, 16, 15, 36 and 37 are connected to the CPU 11 through a CPU bus 10.

The automatic analyzer further includes a sample disk 29 on which sample vessels 41 carrying samples to be analyzed are arranged a reaction disk 22, a sample pipetting mechanism 30 for distributively injecting samples from the sample vessels 41 into reactors 35 arranged on the reaction disk 22, a reagent disk 27 on which reagent vessels 26 are arranged, and a reagent pipetting mechanism 24 for distributively injecting reagents from the reagent vessels 26 into the reactors 35.

The automatic analyzer further includes a distributive sample suction and injection mechanism 19 for sucking samples into the sample pipetting mechanism 30 and injecting the samples into the reactors 35, and a distributive reagent suction and injection mechanism 17 for sucking reagents and injecting the reagents into the reactors 35. The automatic analyzer further includes a stirring mechanism 23 for stirring samples and reagents placed in the reactors 35, a photometer 20 for measuring the change of absorbance of reagents and samples reacted, a light source 25 therefor, a thermostat or isothermal tank 28 for keeping the reactors 35 isothermal or at a constant temperature, a washing mechanism 21 for cleaning the reactors 35 in which analysis is completed, and a washing water supply 18 for supplying cleaning water to the washing mechanism 21 and sucking in waste fluid.

The automatic analyzer further includes a transmitter section 38 by which information given by the control CPU 11 through the CPU bus 10 is transmitted through wireless to a transceiver 40, 42 or 44, and a receiver section 39 for receiving an instruction signal from the transceiver 40, 42 or 44 and supplying the instruction signal to the CPU 11 through the CPU bus 10. The transceivers 40, 42 and 44 include message display portions 40B, 42B and 44B, and operation portions 40E, 42E and 44E, respectively. These transceivers 40, 42 and 44 are small in size so as to be portable, so that different persons on duty carry these receivers, respectively. For example, the transceiver (1) 40 is carried by an apparatus operator, the transceiver (2) 44 is carried by a person in charge of test data, and the transceiver (3) 42 is carried by a person in charge of apparatus maintenance.

In ordinary analysis, samples are placed in the sample vessels 41 and set on the sample disk 29. The samples in the sample vessels 41 are sucked in by the sample pipetting mechanism 30 and the sampling station 19 and injected into the reactors 35. Then, necessary reagents are distributively injected into the reactors 35 from the reagent vessels 26 on the reagent disk 27 by the reagent pipetting mechanism 24 and the reagent dispensing station 17. Then, samples and reagents in the reactors 35 are stirred by the stirring mechanism 23 and reacted with each other.

The thus reacted samples in the reactors 35 are measured by the photometer 20, then measurement results are digitized by the LOG amplifier and A/D converter 12 and fetched into the memory 13 through the CPU bus 10. All these operations are controlled by the control CPU 11, so that analysis results are subjected to an arithmetic operation process and stored in a floppy disk 14 and, at the same time, analysis results are displayed on the CRT display 36 and printed by the printer 37.

Figure 3:
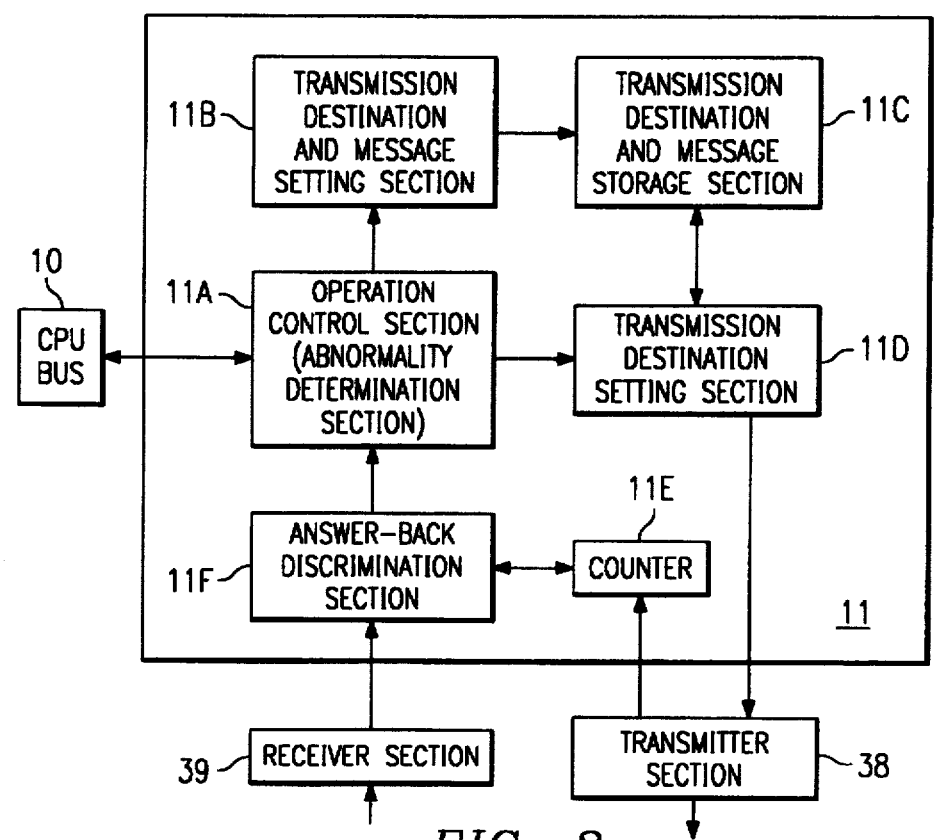
FIG. 3 is a functional block diagram of a control CPU in the embodiment of FIG. 1.

FIG. 3 is a functional block diagram of the control CPU 11.

In FIG. 3, an operation control section 11A not only controls the aforementioned sample measurement operation but also determines whether there is any failure in each section of the automatic analyzer or not. When the operation control section determines that there is any failure, a signal indicating the contents of the failure is supplied to a destination setting section 11D. The transmission destination setting section 11D extracts a transmission destination and a message correspondingly to the thus supplied contents of the failure from a transmission destination and message storage section 11C in which messages classified by transmission destinations are stored. In the storage section 11C for storing messages for every transmission destination, the transmission destinations, that is, transceivers 40, 42 and 44, and the messages for every content of failure are set and stored in advance by a transmission destination and message setting section 11B.

The message picked out from the storage section 11C is supplied, together with a transmission destination code (ID code) indicating a transmission destination, to the transmitter section 38 from the transmission destination setting section 11D. Then, a signal indicating the transmission destination code and the message is sent out from the transmitter section 38. When the signal is sent out from the transmitter section 38, a counting start signal is supplied to a counter 11E from the transmitter section 38.

When the counter 11E starts counting (counting the passage of time), an answer-back discrimination section 11F monitors the content of the counter 11E and at the same time monitors whether any reception signal is supplied from the receiver section 39 or not. When the count value of the counter 11E reaches a predetermined value or not when any reception signal is supplied from the receiver section 39, a corresponding signal is supplied to the operation control section 11A. The operation control section 11A controls the operation of the automatic analyzer in accordance with the signal supplied from the answer-back discrimination section 11F.

Figure 4:
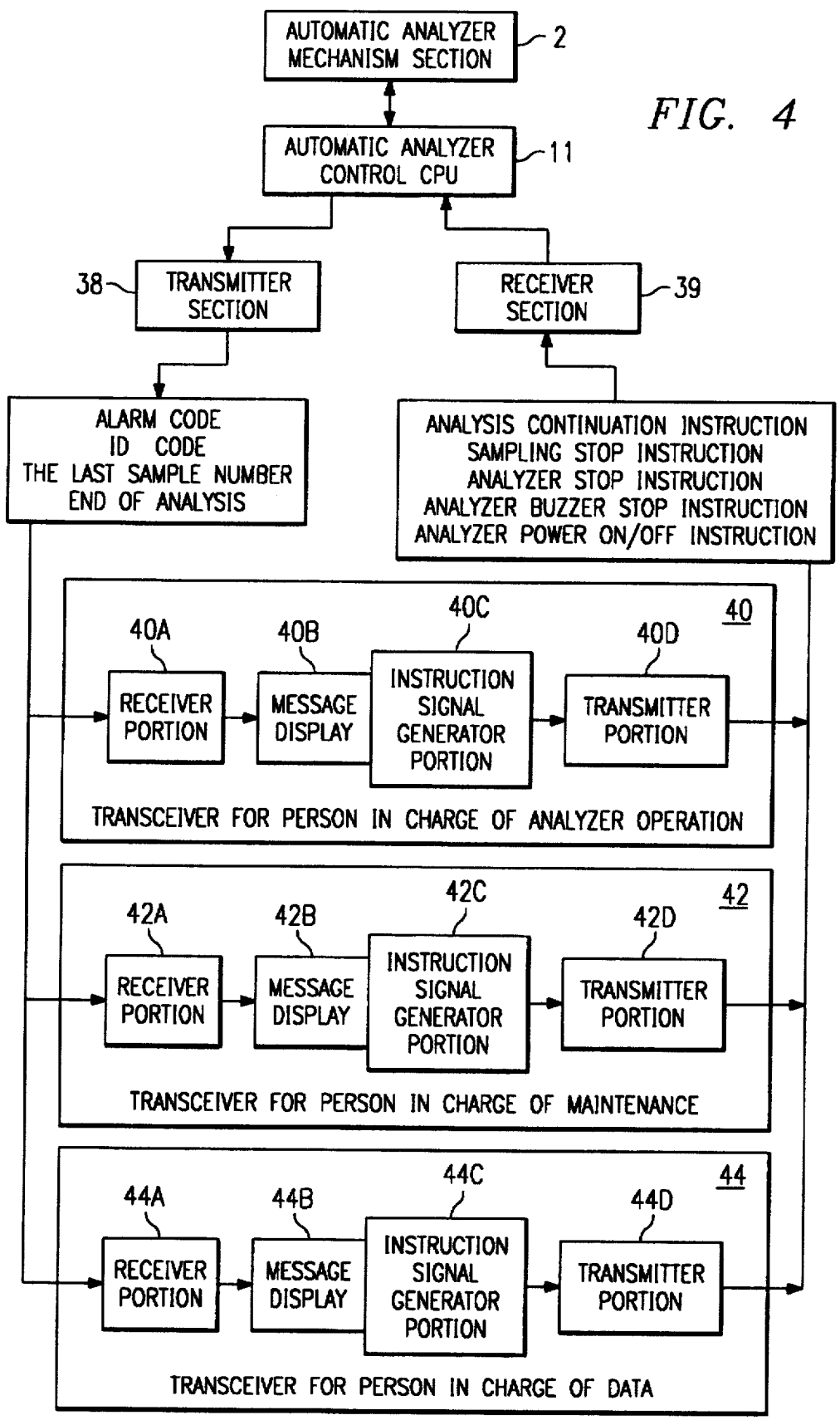
FIG. 4 is a diagram showing schematic functional blocks and a flow of information transmission in transceivers in the embodiment of FIG. 1.

FIG. 4 is a diagram showing schematic functional blocks and a flow of information in the transceivers 40, 42 and 44. The transceivers 40, 42 and 44 include the receiver portions 40A, 42A and 44A, message display portions 40B, 42B and 44B, instruction signal generation portions 40C, 42C and 44C, and transmitter portions 40D, 42D and 44D, respectively.

The transmitter section 38 sends out a signal indicating an alarm code (message code), ID codes (ID code for identifying the automatic analyzer and ID code for identifying the transceiver), the number of the sample in which sampling is completed, and so on. Each of the receiver portions 40A, 42A and 44A of the transceivers 40, 42 and 44 determines whether the received ID code is coincident with the ID code registered in the receiver portion or not. When the received ID code is coincident with the registered ID code, the received signal is supplied to the message display portion. When, for example, the ID code is coincident with the ID code for identifying the transceiver 40, the receiver section 40A supplies the received signal to the message display portion 40B. The message display portion 40B displays a message corresponding to the alarm code. At the same time, the transceiver 40 generates a reception sound (from a reception sound generation portion which is not shown).

When the apparatus operator has confirmed the reception sound, the operator operates the operation portion to make a suitable instruction. This is performed by operating a key indicating an instruction code corresponding to the operation since instructions and instruction codes corresponding thereto are set in advance in the operation portion. When a key indicating an instruction code corresponding to the instruction is operated, the instruction signal generation portion 40C supplies a signal corresponding to the instruction code corresponding to the operated key to the transmitter portion 40D. Then, the transmitter portion 40D sends out a signal indicating the ID code for identifying the automatic analyzer to which the signal is to be transmitted and the contents of the instruction such as instruction to continue analysis, instruction to stop sampling, instruction to stop the operation of the apparatus, instruction to stop the buzzer sound of the analyzer, instruction to switching on/off the electric power source of the analyzer, or the like.

Upon reception of the signal sent out from the transmitter portion 40D, the receiver section 39 determines whether the automatic analyzer ID code contained in the reception signal is coincident with the ID code for identifying its own apparatus or not. When it is determined that these ID codes are coincident with each other, the received signal is supplied to the control CPU 11. Then, the control CPU 11 controls the operation of the automatic analyzer mechanism section 2 in accordance with the signal given from the receiver section 39.

FIG. 5 is a flow chart used for explaining the operation of the CPU 11 shown in FIG. 3.

In step 100 in FIG. 5, the operation control section 11A controls an analysis operation and at the same time determines whether an alarm is to be generated or not (a state to be transmitted has occurred or not), that is, whether there is no occurrence of abnormality. When it is determined that there is no occurrence of abnormality, the process returns to the step 100. When it is determined that abnormality has occurred in the step 100, the transmission destination setting section 11D determines whether the alarm is an alarm to be transmitted to a transceiver located in a remote place or not in step 101. If it is determined that the alarm is not an alarm to be transmitted, the process returns to the step 100. If it is determined in the step 101 that the alarm is an alarm to be transmitted, the process proceeds to step 102 in which the transmission destination setting section 11D searches the storage section 11C to extract a transmission destination (located in a remote place) and a message to be transmitted.

In the next step 103, the transmission destination setting section 11D makes the transmitter section 38 send out a signal indicating the ID code (transmission source code) for identifying the automatic analyzer to which the transmission destination setting section 11D itself belongs, the ID code for identifying the transmission destination and the transmission message and, at the same time, makes the counter 11E start counting. Succeedingly, in step 104, the answer-back discrimination section 11F determines whether the answer-back signal has been received by the receiver section 39 or not. When it is determined that the answer-back signal has not been received yet, the process proceeds to step 106 in which the count value of the counter 11E is confirmed.

Then, in step 107, the answer-back discrimination section 11F determines whether the count value of the counter 11E reaches a set value or not, that is, whether or not a set time has passed after the transmitter section 38 transmitted a signal. When it is determined that the set time has not passed yet, the process returns to the step 104. When it is determined in the step 107 that the set time has passed, the process proceeds to step 108. In the step 108, the answer-back discrimination section 11F transmits to the operation control section 11A the fact that the answer-back signal could be not received though the set time has passed.

Then, the operation control section 11A makes the automatic analyzer operate in accordance with a preliminarily set instruction. That is, when, for example, the abnormality is a failure in the printer, the analysis is terminated or continued after the fact that the printer is abnormal is stored in the memory. Then, the process returns to the step 100. When in the step 104 it is determined that the answer-back signal has been received, the process proceeds to step 105 in which the operation control section 11A makes the automatic analyzer operate on the basis of the answer-back signal. Then, the process returns to the step 100.

FIG. 6 is a view showing an example of messages stored in the storage section 11C for storing messages for every transmission destination. In FIG. 6, alarm names (abnormality names) and codes, messages and transmission destinations corresponding to the alarm names are shown. It is to be understood from FIG. 6 that suitable persons in charge vary in accordance with the contents of abnormality.

Although FIG. 6 shows the case where abnormality to be transmitted to the person in charge of test data includes no abnormality but abnormality of calibration data and abnormality of control data, all abnormality to be transmitted to the operator and the person in charge of maintenance may be transmitted to the person in charge of test data.

Further, the completion of distributive sample suction and injection and the completion of analysis are described as alarm names in FIG. 6 but it is a matter of course that these do not indicate abnormal operations. That is, FIG. 6 shows the fact that these messages are transmitted to transceivers in the same manner as abnormal operations.

FIG. 7A–C shows examples of messages displayed on the message display portions 40B, 42B and 44B of the transceivers 40, 42 and 44 which receive alarms or the like transmitted by automatic analyzers.

FIG. 7A shows the case where the fact that shortage of reagents, abnormality of calibration data and failure in stirring mechanism have occurred in the condition in which sampling of sample number 83 has been completed is transmitted to the person in charge of data from an automatic analyzer A. FIG. 7B shows the case where the fact that shortage of samples has occurred in the condition in which sampling of sample number 115 has been completed is transmitted to the apparatus operator from an automatic analyzer B.

FIG. 7C shows the case where the fact that failure in reaction table has occurred is transmitted to the person in charge of maintenance from an automatic analyzer A and, at the same time, the fact that failure in sample syringe has occurred is transmitted to the person in charge of maintenance from an automatic analyzer B.

The case where the transceiver 44 receives abnormality of calibration data for the person in charge of test data will be described now by way of example.

Abnormality of calibration data is classified into a calibration curve generation impossible alarm (code 2-A in FIG. 6) generated when calculation is made impossible in the middle of a calibration arithmetic operation, an alarm (code 2-B) generated when a plurality of measured values of calibration data vary widely, an alarm (code 2-C) generated when the difference between the previous calibration value and the current calibration value is larger than an allowable set value, and an abnormal sensitivity alarm (code 2-D) generated when the sensitivity of calibration is lower than an allowable set value.

The case of transmission of an alarm indicated by code 2-A means the fact that calibration did not succeed with respect to a certain item of analysis items subjected to calibration. Accordingly, it is necessary that the person in charge of test data instructs the apparatus operator to retry calibration with respect to the failure item or retry to examine a general patient subject to be tested with respect to analysis items concerned.

In the case of execution of a plurality of analyses, calibration for all analysis items do not always fail. Accordingly, because there is no necessity of immediately stopping the operation of the apparatus in which abnormality of calibration data has occurred, an instruction to continue analysis is transmitted to the receiver section 39 of an automatic analyzer by operating the transceiver 44. Upon reception of this instruction, the control CPU 11 of the automatic analyzer continue the operation of the automatic analyzer.

In the case where an alarm indicated by code 2-B is transmitted, reliability of data at the time of the generation of a calibration curve comes into a problem. From the point of view of data, analysis for other analysis items than the analysis item in which a problem has occurred may be executed without any special trouble or a problem may be caused by a sudden failure in a part of analysis data. Accordingly, the person in charge of test data operates the transceiver 44 so that an instruction signal to continue the operation of the apparatus is transmitted to the receiver section 39 of the automatic analyzer. When the receiver section 39 receives the instruction signal from the transceiver 44, the control CPU 11 of the automatic analyzer continues the analysis operation of the apparatus.

In this case, the person in charge of test data immediately confirms calibration data on the analyzer. When the cause of abnormality of data is clear so that a determination is made that analysis can be continued without hindrance, the previous instruction is continued. On the contrary, when the confirmation of data results in a conclusion that there is some hindrance in continuation of analysis, an instruction is given to the apparatus operator to retry calibration with respect to items concerned or retry examinations with respect to analysis items concerned. Further, because there is much possibility that bubbles or the like are apt to be mixed in the flow path of the apparatus, an instruction is given to the apparatus operator to carry out cleaning of the flow path sufficiently after the stopping of the apparatus.

In the case where an alarm indicated by code 2-C is transmitted, a calibration curve is generated on the basis of a determination as to whether there is any condition different from conditions in the previous case. In the case where the cause of abnormality is clear so that a determination is made that analysis can be continued without hindrance, such as the case where newly prepared reagents are used, the case where a reference solution having a concentration different from that in the previous case is used, or the like, the person in charge of test data operates the transceiver 44 to transmit an instruction signal to the receiver section 39 of the automatic analyzer to continue the analysis without any change. When the receiver section 39 receives the instruction signal, the control CPU 11 of the automatic analyzer continues the analysis operation.

When the cause is not clear contrariwise to the aforementioned case, there is occurrence of somewhat trouble in the generated calibration curve. Also in this case, the person in charge of test data transmits an instruction signal to the automatic analyzer to continue the operation of the apparatus without any change. At the same time, the person in charge of test data examines the cause of the trouble.

The transmission of an alarm indicated by code 2-D means the fact that there is no reliability on the generated calibration curve. The person in charge of test data operates the transceiver 44 to transmit an instruction signal to the automatic analyzer to continue the operation of the apparatus without any change. Because a determination is however made that there is any hindrance to continuation of analysis for items concerned, the person in charge of test data prepares reagents, reference solutions, and so on, newly and then gives an instruction to the apparatus operator to try calibration for items concerned or retry examinations for analysis items concerned.

Even in the case where any one of the aforementioned alarms is generated, the person in charge of test data may operate the transceiver 44 to transmit an instruction signal to the receiver section 39 to stop the operation of the automatic analyzer if a determination is made that there is any hindrance to continuation of analysis in the condition in which analysis for a single analysis item is carried out. When the instruction signal is received by the receiver section 39, the control CPU 11 stops the analysis operation.

Further, after confirmation of occurrence of a trouble in the apparatus on the basis of alarm indication on the transceiver 40, the apparatus operator located in a remote place from the automatic analyzer stops the alarm (buzzer sound) of the body of the automatic analyzer by using the transceiver while the apparatus operator stays in the remote place. Alternatively, the apparatus operator may give an instruction to the body of the automatic analyzer by using the transceiver 40 so that the analysis is continued regardless of the generation of an alarm until the apparatus operator arrives at the automatic analyzer side.

Further, the apparatus operator can stop the operation of the body of the automatic analyzer or can switch off the electric source of the body of the automatic analyzer from a remote place as an emergency countermeasure immediately after the confirmation of the generation of an alarm without the necessity of confirmation of the state of the automatic analyzer. Further, because the apparatus operator can switch on the electric source of the body of the automatic analyzer from a remote place by using the transceiver 40, the electric source of the body of the automatic analyzer can be switched on immediately after the determination of the starting of analysis without waiting for the operator's actual arrival at the apparatus side. Accordingly, because steady-state preparation work such as heating of the reaction isothermal tank, preparatory cleaning of the reactors, priming of syringes and pipettes, and so on, prepared for the starting of the operation of the apparatus can be completed automatically into a standby state before the operator's arrival at the analyzer, the analyzing work can be carried out immediately after the operator's arrival.

With respect to the person in charge of maintenance, like the person in charge of test data and the apparatus operator, a suitable instruction signal for stopping the buzzer sound, switching off the electric source of the apparatus, or the like, is transmitted to the automatic analyzer on the basis of the contents displayed on the transceiver 42.

With respect to the contents to be transmitted to the transceiver 40, 42 or 44 from the automatic analyzer, requests may vary in accordance with facilities such as hospitals, test centers, research laboratories, and so on. For example, in the case of a facility in which an automatic analyzer having an attachment for electrolytic analysis is installed, alarms (alarm codes 23 and 24 shown in FIG. 6) for abnormality of data concerned with electrolytic analysis and for abnormality caused by the attachment are required. On the contrary, in the case of a facility in which an automatic analyzer having no attachment for electrolytic analysis is installed, the aforementioned alarms are not required. Further, there may be considered the case where only one transceiver is provided initially to receive all messages and then transceivers are provided additionally.

In an embodiment of the present invention, therefore, transmission alarms corresponding to the contents of abnormality of the automatic analyzer and transmission destinations thereof can be set in accordance with the facility as occasion demands.

That is, in FIG. 3, a signal indicating a transmission alarm, an alarm code and a transmission destination is supplied to the control CPU 11 through the CPU bus 10 from a keyboard or the like by the operator. The signal indicating the transmission alarm, alarm code and transmission destination supplied to the CPU 11 is supplied to the section 11B in which messages are set for every transmission destination, through the operation control section 11A. The section 11B for setting messages for every transmission destination causes the transmission destination message storage section 11C to store the transmission message, alarm code and transmission destination thus supplied.

FIG. 8 shows an example of an operation screen displayed on the CRT 36 in the case where the transmission message, alarm code and transmission destination are to be set.

In FIG. 8, "CODE" represents an alarm code, "INDICATE" represents a message displayed on a transceiver, and "RECEIVER" represents an ID code for identifying the transceiver. In this example, ID code "1" indicates a transceiver for an apparatus operator, ID code "2" indicates a transceiver for a person in charge of test data, and ID code "3" indicates a transceiver for a person in charge of maintenance of the apparatus. Incidentally, correspondence between the alarm codes and the contents of abnormality is stored in the storage section 11C in advance. In addition, the ID code for identifying the transceiver can be set by operating an operation portion (not shown) of the transceiver.

In this manner, necessary messages and transmission destinations can be set in accordance with the facility in which an automatic analyzer is installed. Further, the invention can be applied to the case where there is no transceiver or only one transceiver required initially after the installation of the automatic analyzer and then transceivers are provided additionally.

As described above, according to an embodiment of the present invention, not only a suitable transmission destination remote from a body of the automatic analyzer is selected in accordance with the contents (the contents of abnormality and the progressive state of the operation) to be transmitted so that the contents are transmitted to the selected transmission destination, but also a suitable operation control instruction is received from a suitable person in charge. Accordingly, a suitable control operation can be carried out rapidly so that the analysis operation interruption time can be shortened. Thus, an automatic analyzer improved in analyzing efficiency can be provided.

Further, according to an embodiment of the present invention, messages to be transmitted and transmission destinations can be set arbitrarily. Accordingly, necessary messages and transmission destinations can be set in accordance with the facility in which an automatic analyzer is installed. Further, the invention can be applied to the case where there is no transceiver or only one transceiver required initially after the installation of the automatic analyzer and then transceivers are provided additionally.

Further, according to an embodiment of the present invention, the analyzing operation is controlled in accordance with a preliminarily set instruction when there is no instruction signal received from a transmission destination within a predetermined time after the transmitter section of the automatic analyzer transmits a transmission message to the transmission destination. Accordingly, even in the case where a trouble has occurred in the transmission destination, a suitable control operation can be carried out.

Figure 9:
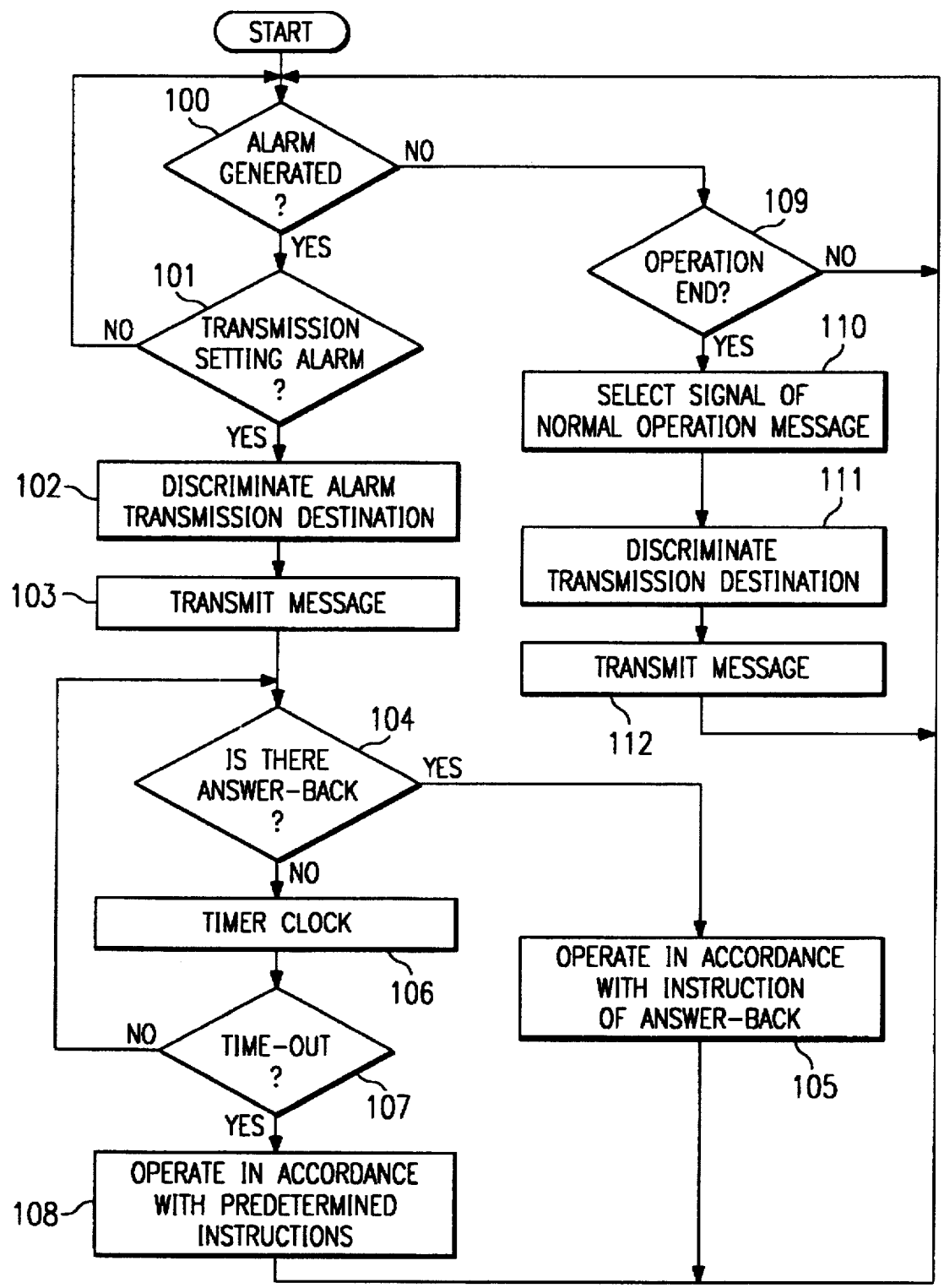
FIG. 9 is an operational flow chart in another embodiment of the present invention.

FIG. 9 is an operational flow chart of another embodiment of the present invention. The structure of the embodiment shown in FIG. 9 is the same as that shown in FIGS. 1 to 4 and the description thereof will be omitted.

The embodiment shown in FIG. 9 is substantially equal to the embodiment shown in FIG. 5, except that the flow chart of FIG. 9 is formed by adding steps 109 to 112 to the flow chart of FIG. 5.

In step 100 in FIG. 9, the operation control section 11A determines whether abnormality has occurred in the automatic analyzer or not. When it is determined that there is no occurrence of abnormality, the process proceeds to step 109. In the step 109, the operation control section 11A determines whether one operation of the automatic analyzer body has been completed or not. The one operation means, for example, an operation of injecting a sample into a reactor or an operation of injecting a reagent into a reactor. When it is determined that the one operation has not been completed yet, that is, when the one operation is in execution, the process returns to the step 100.

When in the step 109 it is determined that the one operation has been completed, the process proceeds to step 110. In the step 110, the operation control section 11A supplies an instruction signal to the transmission destination setting section 11D to select a normal operation message (not only indicating the fact that the operation is normal but also indicating the progressive state of the operation) stored in the storage section 11C in advance. In the next step 111, the transmission destination setting section 11D discriminates the normal operation message stored in the storage section 11C in advance, on the basis of the transmission destination.

Succeedingly, in step 112, a signal indicating the ID code for identifying the transceiver of the transmission destination, the ID code for identifying the automatic analyzer of the transmission source and the message indicating the fact that the operation is normal is sent out from the transmitter section 38. Then, the process returns to the step 100.

Upon reception of the normal operation message signal, the transceiver generates a sound different from the sound generated at the time of the occurrence of abnormality. Then, a message indicating the fact that the operation is normal is displayed on the display portion of the transceiver. In this case, messages which vary in accordance with the operations can be displayed so that the progressive state of the operation can be indicated.

As described above, according to the other embodiment of the present invention, the same effect as in the embodiment shown in FIG. 5 can be obtained.

Furthermore, according to the other embodiment of the present invention, because the fact that the automatic analyzer is normal is transmitted to a transceiver located remotely so that a message not only indicating the fact that the operation is normal but also indicating the progressive state of the operation is generated, respective persons in charge located in remote places can monitor analysis progress information (can recognize the fact the analyzing operation is in progress normally).

Although the invention is configured so that a determination is made in the step 109 of the embodiment in FIG. 9 as to whether one operation has been completed or not, the invention may be configured so that a determination is made as to whether a predetermined time instead of one operation has passed or not. That is, the invention can be configured so that messages are displayed on the transceiver at intervals of a predetermined time as long as the analyzing operation is normal.

Further, in the aforementioned embodiment, the transceiver can perform transmission/reception in one facility such as a hospital, or the like, in which the automatic analyzer is installed.

Further, the signal exchange between the transmitter/receiver section of the automatic analyzer and each transceiver may be performed by wire or by wireless. In the case where the signal exchange is performed by wireless, infrared rays or the like can be used besides electric wave.

Further, in the embodiment in FIG. 5, a request to transmit the progressive state of the operation may be transmitted to the automatic analyzer side from the transceiver side so that the progressive state of the operation can be transmitted to the transceiver from the automatic analyzer side in accordance with the request.

Further, in the case where the unmanned operation of the automatic analyzer is to be carried out at midnight or the like, the invention may be configured so that the persons in charge carry portable receivers using telephone circuits and exclusively used for reception, besides the aforementioned transceivers.

Although the aforementioned embodiments show the case where three transceivers are used, the invention can be applied to the case where one transceiver, two transceivers or four or more transceivers are used.

The present invention configured as described above has the following effects.

Not only a suitable transmission destination remote from the body of the automatic analyzer is selected in accordance with the contents to be transmitted so that the contents are transmitted to the selected transmission destination, but also a suitable operation control instruction is received from a suitable person in charge. As a result, a suitable control operation is carried out rapidly so that the analyzing operation interruption time can be shortened. Thus, an automatic analyzer improved in analyzing efficiency can be provided.

Further, a determining section controls the analyzing operation in accordance with a predetermined instruction when there is no instruction signal received from a transmission destination within a predetermined time after the transmitter section of the automatic analyzer transmits a transmission message to the transmission destination. Accordingly, even in the case where a trouble has occurred in the transmission destination, a suitable control operation can be carried out.

Further, states to be transmitted and transmission messages are stored in the message storage section by the transmission message setting section in accordance with the operator's operation. Accordingly, message transmission can be performed in accordance with requests from respective facilities in which automatic analyzers are installed.

Further, the transmission destination discrimination section discriminates the normal operation message (abnormality message) and the transmission destination whenever a predetermined process of the analyzing operation is completed or at intervals of a predetermined time. A signal indicating the transmission destination and the normal operation message (abnormality message) thus discriminated is sent out from the transmitter section. Accordingly, the person in charge in the transmission destination can recognize the fact that the analyzing operation is in progress normally or the fact that abnormality has occurred.

What is claimed is:

1. An automatic analyzer communication system for use with an automatic analyzer, the system comprising:
an automatic analyzer;
a central processing unit;
an operational control section which controls the operation of sample measurements performed by the automatic analyzer, monitors the progressive state of analysis, and detects the occurrence of an abnormality in the automatic analyzer;

a message setting section which retrieves a transmission message corresponding to the type of abnormality detected by the operational control section, said transmission message being retrieved from a transmission message storage section in response to a signal from the operational control section, wherein said transmission message storage section comprises at least one transmission message classified by transmission destination and electronically stored;

a transmission destination setting section which retrieves a transmission destination from a transmission destination storage section wherein every transmission destination and type of abnormality detected by the operational control system are stored, and which is responsive to the transmission message retrieved by the message setting section;

a transmitter which transmits a signal responsive to the retrieved transmission destination and the transmission message retrieved by the message setting section in response to the type of abnormality detected by the operational control section, the signal having an alarm code, an analyzer identification code and a transceiver identification code;

a transceiver, having a registered identification code, which receives the signal from the transmitter if the transceiver identification code is coincident with the registered identification code, the transceiver further comprising: a display which displays a message corresponding to the alarm code, a means for selecting an instruction code from a plurality of predetermined instruction codes, and a means for transmitting a signal responsive to the selected instruction code and the analyzer identification code;

a receiver which receives the signal for the transceiver;

an answer-back discrimination section in communication with the receiver, the answer-back discrimination section being responsive to the analyzer identification code, wherein the answer-back discrimination section provides the selected instruction received from the transceiver to the operational control section which causes the analyzer to operate in accordance therewith, and provides a set time passed signal to the analyzer which causes the analyzer to operate in accordance therewith if a counter indicates a set time period has lapsed since the transmission of the transmission message.

* * * * *